United States Patent
Horiuchi et al.

(10) Patent No.: US 11,388,864 B2
(45) Date of Patent: Jul. 19, 2022

(54) **METHOD OF PRODUCING *LACTUCA* PLANT SEED USING A MEGACHILE BEE**

(71) Applicant: SAKATA SEED CORPORATION, Yokohama (JP)

(72) Inventors: Shingo Horiuchi, Kanagawa (JP); Takao Suzuki, Kanagawa (JP); Atsushi Izumida, Kanagawa (JP)

(73) Assignee: SAKATA SEED CORPORATION

( * ) Notice: Subject to any disclaimer, the term of this patent is extended or adjusted under 35 U.S.C. 154(b) by 0 days.

(21) Appl. No.: 16/770,131

(22) PCT Filed: Dec. 5, 2018

(86) PCT No.: PCT/JP2018/044797
§ 371 (c)(1),
(2) Date: Jun. 5, 2020

(87) PCT Pub. No.: WO2019/111975
PCT Pub. Date: Jun. 13, 2019

(65) Prior Publication Data
US 2020/0352114 A1    Nov. 12, 2020

(30) Foreign Application Priority Data
Dec. 6, 2017    (JP) .............................. JP2017-234674

(51) Int. Cl.
*A01G 22/15*    (2018.01)
*A01G 22/60*    (2018.01)
(Continued)

(52) U.S. Cl.
CPC .............. *A01G 22/15* (2018.02); *A01G 7/00* (2013.01); *A01G 22/60* (2018.02); *A01H 1/02* (2013.01);
(Continued)

(58) Field of Classification Search
None
See application file for complete search history.

(56) References Cited

U.S. PATENT DOCUMENTS

2008/0072353 A1    3/2008    Gibson et al.
2009/0271897 A1*   10/2009   Gibson .................... A01H 5/12
                                                          800/305
2010/0306882 A1    12/2010   Michel

FOREIGN PATENT DOCUMENTS

AU    2015-200033 A1    2/2015
CN       105519401 A    4/2016
(Continued)

OTHER PUBLICATIONS

Lebeda et al. "Wild and weedy *Lactuca* species, their distribution, ecogeography and ecobiology in USA and Canada". Genet Resour Crop Evol. 2012. 59:1805-1822. (Year: 2012).*

(Continued)

*Primary Examiner* — Matthew R Keogh
*Assistant Examiner* — David R Byrnes
(74) *Attorney, Agent, or Firm* — Harness, Dickey & Pierce, P.L.C.

(57) ABSTRACT

A method is provided of producing a *Lactuca* plant seed including using a *Megachile* bee as pollination means, and providing the a *Megachile* bee a minor nectar plant to have preference in flower visiting, in addition to a pollen parent *Lactuca* plant and a seed parent *Lactuca* plant and to perform a crossing of a *Lactuca* plant using a plant species having the preference in flower visiting equivalent to or lower than that of the *Lactuca* plant. According to one embodiment, it is possible to produce a *Lactuca* hybrid plant seed more efficiently and economically than before while using a *Megachile* bee as pollination means.

17 Claims, 3 Drawing Sheets

(51) Int. Cl.
| | |
|---|---|
| *A01H 6/14* | (2018.01) |
| *A01G 7/00* | (2006.01) |
| *A01H 1/02* | (2006.01) |
| *A01H 5/12* | (2018.01) |
| *A01K 47/00* | (2006.01) |

(52) U.S. Cl.
CPC .............. *A01H 5/12* (2013.01); *A01H 6/1472* (2018.05); *A01K 47/00* (2013.01); *A01K 2227/706* (2013.01); *A01K 2267/00* (2013.01)

(56) References Cited

FOREIGN PATENT DOCUMENTS

| | | |
|---|---|---|
| JP | 2002-247927 A | 9/2002 |
| JP | 3635036 B2 | 3/2005 |
| JP | 2008-167689 A | 7/2008 |
| JP | 2009-539409 A | 11/2009 |
| JP | 4471983 B2 | 6/2010 |
| JP | 5627894 B2 | 11/2014 |
| WO | 2007-049730 A1 | 5/2007 |
| WO | 2007-146420 A2 | 12/2007 |
| WO | 2009-086173 A2 | 7/2009 |

OTHER PUBLICATIONS

Gonzalez et al. "Phylogeny of the bee family Megachilidae (Hymenoptera: Apoidea) based on adult morphology". Systematic Entomology. 37(2): 261-286. (Year: 2012).*
Shivashankara et al. "Diversity of Insect Pollinators and Foraging Behavior of Native Honey Bees on Coriander". Environment and Ecology. 34(4):1315-1319. (Year: 2016).*
Utsunomiya and Nakamura. "Effects of Anthropogenic Disturbances on the Flowering Plant—Insect Pollinator System in Kanazawa Castle Park". Far Eastern Entomologist. 162:1-24. (Year: 2006).*
Donovan. "Interactions between Native and Introduced Beeds in New Zealand". New Zealand Journal of Ecology. 3: 104-116. (Year : 1980).*
Brookes, B.S. "Pollination Studies in Alfalfa, *Medicago sativa* L. (Leguminosae), with Special Reference to the Alfalfa Leafcutter Bee, *Megachile rotundata* (F.) (Apoidea)". Master's Thesis. Carleton University Department of Biology (Year: 1992).*
International Search Report for International Application No. PCT/JP2018/044797 dated Feb. 26, 2019 (2 pages).
S. Ishida et al., "Development of Processing Dedicated F1 Varieties by Improving the Breeding Method of Lettuce F1. 1. Search for Lettuce-Visiting Insects", The Japanese Society for Horticultural Science, Journal of Horticultural Research, vol. 7, Annex 2, Sep. 27, 2008, p. 182, with English translation.
M. Goubara, et al., "Flower Visitors of Lettuce Under Field and Enclosure Conditions", Applied Entomology and Zoology, Nov. 25, 2003, vol. 38, No. 4, pp. 571-581.
International Preliminary Report on Patentability for International Application No. PCT/JP2018/044797 with Written Opinion dated Jun. 9, 2020 (9 pages) with English translation.
"The plot thickens: does low density affect visitation and reproductive success in a perennial herb, and are these effects altered in the presence of a co-flowering species?"; Author—Tracy S. Feldman; Oecologia, Springer, Berlin, DE, vol. 156, No. 4; Published on Apr. 16, 2008; pp. 807-817.
"A preliminary anaslysis of the floral preferences of the alfalfa leafcutting bee, *Megachile rotundata*"; Author—Earnest Small, et al.; Canadian Field Naturalist, Ottawa Filed-Naturalists' Club, CA, vol. 111; Published on Jan. 1, 1997; pp. 445-453.
Supplementary European Search Report issued for the corresponding European Patent Application No. 18887155.2 dated Aug. 13, 2021 (total 10 pages).

* cited by examiner

METHOD OF PRODUCING *LACTUCA* PLANT SEED USING A MEGACHILE BEE

CROSS-REFERENCE TO RELATED APPLICATIONS

This application claims the benefit of priority to Japanese Patent Application No. 2017-234674, filing date: Dec. 6, 2017, the entire contents of which are incorporated herein by reference.

TECHNICAL FIELD

The present invention relates to a method of efficiently producing a *Lactuca* plant seed using a *Megachile* bee as pollination means. More specifically, the present invention relates to a method of producing a *Lactuca* plant seed using a *Megachile* bee as pollination means and using a minor nectar plant in addition to a pollen parent *Lactuca* plant and a seed parent *Lactuca* plant. More specifically, the present invention relates to a method for producing a first filial generation seed (F1 hybrid) of lettuce.

BACKGROUND ART

Plant varieties include open pollinated variety and first filial generation (hereinafter, sometimes abbreviated as "F1") varieties, and in major crops, F1 varieties are widely used.

The F1 varieties have significant advantages such as vigorous growth due to heterosis, fast growth, and improved yield. As a result of the vigorous growth, the F1 varieties can be also expected to have improved pest resistance and improved environmental adaptability such as cold and heat tolerance. In addition, since genotypes of the F1 varieties are both heterogenic and close to identical, phenotypes show extremely high uniformity, such that the marketability of products is enhanced. In addition, useful traits controlled by dominant genes can be accumulated in parents of the F1 varieties which enables rapid breeding of the F1 varieties. Due to the advantages described above, the F1 varieties have become the mainstream of cultivars in major crops.

Plants belonging to the genus *Lactuca*, in particular, lettuce (*Lactuca sativa*) are produced in various countries around the world. Lettuce is a vegetable having a very large market scale and F1 varieties are highly desired. The present inventors have succeeded in developing a cytoplasmic male sterile lettuce necessary for F1 variety development of lettuce and showed that F1 hybrids can be produced in lettuce (WO 2007/049730 A) (Patent Document 1)).

Seed production of lettuce F1 hybrids can be performed by hand pollination. Lettuce only flowers for several hours in the morning, leading to decreased working efficiency, the number of seeds obtained by crossing one flower can be as little as 10 grains. For this reason, seed production by the hand pollination has low economic efficiency and there is much need for a highly economical and efficient seed production method. As is practiced in other crops, it is desirable to develop a highly economical pollen transfer method using a pollinating insect. However, since the *Apis mellifera*, a commonly utilized pollinating insect, does not visit lettuce, there is a need to utilize pollinating insects other than *Apis mellifera*.

In order to solve the before mentioned problems, in lettuce, the utilization of various pollinating insects has been examined.

For example, JP 3635036 B2 (Patent Document 2) discloses a method of seed production of lettuce F1 hybrids using *Lasioglossum* villosultum trichopse. However, *Lasioglossum* villosultum trichopse has a small population, and even if it can be captured, a propagation method thereof is not disclosed. In addition, according to data described in Patent Document 2, the seed production efficiency of the *Lasioglossum* villosultum trichopse can be as small as 330 grains (1000 grain weight of the lettuce is about 1 g, so the *Lasioglossum* villosultum trichopse is about 0.33 g) per plant. Therefore, from an economical perspective, the *Lasioglossum* villosultum trichopse is considered to be difficult to use for commercial seed production. In addition, *Lasioglossum* villosultum trichopse is not available from the market and is generally difficult to obtain, and therefore is considered to be difficult to use for commercial seed production requiring a large number of pollinating insects.

In addition, JP 4471983 B2 (Patent Document 3) discloses a method of seed production of lettus F1 hybrids using *Lucilia sericata*. However, according to the results of the pollination ability test of *Lucilia sericata* disclosed in Patent Document 3, the number of seeds remains in a total of 245 seeds (about 0.245 g) from two plants, and as disclosed in Patent Document 2, the *Lucilia sericata* may be difficult to use for commercial seed production from an economical perspective. Also, since flies do not have homing instinct, the seed production requires a closed facility. In commercial seed production, it is desirable to be able to produce seeds in an open field with low production costs. Therefore, the method of Patent Document 2 may lead to an increase in cost.

JP 5627894 B2 (Patent Document 4) discloses a method of seed production of lettuce F1 hybrids using *Calliphora vomitaria, Calliphora erythrocephala*, or *Lucilia* Caesar, which are members of Calliphoridae in the other Diptera. According to the method of Patent Document 4, 1.67 g to 11.25 g of F1 hybrids per plant of the lettuce can be obtained.

However, as described in paragraph 0040 of Patent Document 4, the Diptera are not insects that normally pollinates flowers of lettuce, but it is not known that the Diptera also feeds on nectar. Patent Document 4 only discloses that the Diptera acts as a pollinator of the lettuce if excessive numbers are introduced into a closed environment. In addition, according to the examination document (written by the applicants) of the examination process of Patent Document 4, the Diptera is not specifically attracted to the lettuce flowers, but it is described that by introducing a large population of Diptera, at least a part of the Diptera stochastically landed at the corolla and came in contact with pollen to achieve pollination. Therefore, in this method, it is necessary to introduce an excessive number of Diptera, since the pollination efficiency is poor compared to pollinating insects who actively visit flowers for foraging. In addition, as in the case of Patent Document 3, since the flies do not have homing ability, seed production requires a closed facility. Therefore, it is likely to lead to an increase in production cost.

JP 2009-539409 A (Patent Document 5) (WO 2007/146420 A) discloses a method of seed production of lettuce F1 hybrids using a *Megachile* bee, specifically, alfalfa leaf cutting bee (*Megachile rotundata*). Here, a method of attracting *Megachile rotundata* to visit a lettuce flower by cultivating alfalfa near the lettuce is disclosed. In addition, in WO 2009/086173 A (Patent Document 6), as in Patent Document 5, a method of seed production of lettuce F1 hybrids using a *Megachile* bee, specifically, alfalfa leaf cutting bee is disclosed.

However, the example of Patent Document 5 only discloses that flowers having 5.6 grains on average are obtained for 24 male sterile flowers (paragraph 0065 in Patent Document 5), 13 different *Megachile* rotundata females are observed every 2 minutes, visiting 7.1 flowers on average every minute (paragraph 0096 in Patent Document 5). Patent Document 5 does not disclose a specific and quantitative amount of seed produced, for example, the yield of the lettuce F1 hybrids per plant and the yield of the F1 hybrids of the lettuce per field area unit. The same is also true for Patent Document 6.

Therefore, it was difficult to consider that those skilled in the art reviewing Patent Document 5 and Patent Document 6 can perform commercial seed production of the lettuce F1 hybrids by using the method disclosed herein.

PRIOR ART LIST

Patent Document

Patent Document 1: WO 2007/049730 A
Patent Document 2: Japanese Patent Publication No. 3635036 (JP 3635036 B2)
Patent Document 3: Japanese Patent Publication No. 4471983 (JP 4471983 B2)
Patent Document 4: Japanese Patent Publication No. 5627894 (JP 5627894 B2)
Patent Document 5: Japanese Patent Application Laid-Open Publication No. 2009-539409 A (JP 2009-539409 A (WO 2007/146420 A))
Patent Document 6: WO 2009/086173 A

SUMMARY OF THE INVENTION

Problems to be Solved by the Invention

An object of the present invention is to provide a more efficiently and economically feasible method for producing a *Lactuca* plant seed than before using a *Megachile* bee as the means of pollination.

Means for Solving Problems

An alfalfa leaf cutting bee is the most widely used pollinator for seed production of alfalfa in North America (Reference Document 1 (W. P. KEMP et al., (2000)), p904). In addition, the alfalfa leaf cutting bee is also known as a pollinator of crops other than alfalfa, specifically, Blueberries, Borage, Canola, Carrot, Cranberries, Crown vetch, Hairy vetch, Mint, Onion, and Sweet vetch (Reference Document 2 (Eric Mader et al., (2010)), p10, Table 1.2). The alfalfa leaf cutting bee has excellent characteristics (univoltinism, sequential allogeneic flower visiting ability, high pollination efficiency, ease of management, nesting ability adapted to artificial environment) as a pollinator (Reference Document 3 (Matsuoka Mitsuo, "Insect Utilization Science Series 7" (1996), p99).

Bees, such as the alfalfa leaf cutting bee need to collect pollen or nectar for their offspring, resulting in high pollination efficiency regardless of species. On the other hand, parent flies only lay eggs and the offspring larvae are left to forage from putrefactive matters and the like, such that the parent flies only need to collect nectar as a nutrient source for producing its own energy and eggs.

In the case of the bees, since parent bees need to collect and provide a nutrient source until the offspring becomes an adult, a large amount of honey and pollen per offspring are required. In particular, in the case of the solitary bee, the next generation's breeding depends on the work of the parent bees, so the bee tries to achieve the next generation's breeding in a short period of time. For this reason, in the bees, the activity of one individual is remarkable, which shows 20 to 80 times that of social honeybees.

Thus, the alfalfa leaf cutting bee has a very high ability as a pollinator and is considered to be a promising replacement to honeybees as a pollinator for various crops. In addition, alfalfa seed production of the alfalfa is mainly performed in the western United States, and the alfalfa leaf cutting bee is produced in Canada, then imported into the United States in large quantities every year. Since the major lettuce seed production area is also the western United States, it is advantageous in that a large amount of alfalfa leaf cutting bee can be easily available.

The alfalfa leaf cutting bee has been reported to be a euryphagous species that visit flowers of a wide range of asteraceae plants, but has strong preference to leguminous plants (Reference Document 4 (Dave Goulson, Annu. Rev. Ecol. Evol. Syst. 34:1-26 (2003)), p3).

In the method from Patent Document 5 (JP 2009-539409 A) described above, alfalfa is used as an attractive plant. However, since the alfalfa leaf cutting bee prefers to visit alfalfa over the lettuce, when the companion planting of lettuce and alfalfa is made, the alfalfa leaf cutting bee will favor visiting the alfalfa. As a result, the seed production had to be limited due to the lack of efficiency of pollination.

Patent Document 5 (paragraph 0048) further discloses that after the lettuce plant flower, it is possible to cut off the flowers of the alfalfa so that the alfalfa leaf cutting bee concentrates on the lettuce.

However, there is a risk that cutting off the flowers of the alfalfa will cause the following serious problems.

Since lettuce flowers have a special flowering habit causing flowers to open early in the morning and close after a few hours, if the flowers of the alfalfa are cut off, after lettuce flowers are closed, all nectar sources are lost from the seed production field. On the other hand, if the temperature is about 25° C. or higher, the alfalfa leaf cutting bee tries to continue the foraging activities all day long. For this reason, the active flight to find the honey source is repeated, and most individuals consume their physical strength, and if the honey source is insufficient, they starve to death during the day. Therefore, as described above, if the nectar source is not present in the seed production field after closing the flowers of the lettuce by cutting off the flowers of the alfalfa, the alfalfa leaf cutting bee will starve to death.

In addition, cutting off the flowers of all alfalfa in the seed production field every time the alfalfa leaf cutting bee is released is cumbersome and requires a great deal of labor cost.

As described above, lettuce has a special flowering habit. Flowers are only open for a few hours in each morning, but as is also described in Patent Document 2 (paragraph 0006), many pollinating insects have a diurnal flower visiting pattern which performs the foraging activity for a long time.

For this reason, it was difficult to intensively perform the foraging activity of the pollinating insect on a specific plant for a short time during the morning.

In addition, Patent Document 5 described above discloses that in addition to using alfalfa as the attractive plant, a plant extract containing a plant composition that attracts the alfalfa leaf cutting bee is placed in the vicinity of lettuce or in contact with the lettuce. However, such an attractive extract effective for the alfalfa leaf cutting bee is not actually reported, and is not specifically disclosed in Patent Document 5. For this reason, it was difficult for those skilled in the art to easily obtain and use such an attractive extract.

Under these circumstances, the inventors have repeatedly made an intensive examination.

The present inventors have now examined preparing the pollen parent *Lactuca* plant and the seed parent *Lactuca* plant in the seed production field of the *Lactuca* plant when producing the *Lactuca* plant seed, and performing the crossing of the *Lactuca* plant using the *Megachile* bee as the pollination means. At this time, in order to prevent a bee from being in a starved state when the flowers of the *Lactuca* plant are closed, a minor nectar plant was utilized when crossing the *Lactuca* plant using the *Megachile* bee as the means of pollination. The ideal minor nectar plant is a plant species in which the *Megachile* bee prefers to visit less than or equally as much as the *Lactuca* plant. As a result, it is possible to prevent the leaf cutting bee from being in a starved state by utilizing a minor nectar plant. Hybrid seed production of the *Lactuca* plant can be performed with increased efficiency.

The present invention is based on the findings described above.

That is, according to the present invention, the following inventions are provided.

<1> A method of producing a *Lactuca* plant seed comprising: using a *Megachile* bee as pollination means; and providing the *Megachile* bee a minor nectar plant to have preference in flower visiting, in addition to a pollen parent *Lactuca* plant and a seed parent *Lactuca* plant and to perform a crossing of a *Lactuca* plant using a plant species in which the preference in flower visiting is equivalent to or less than that of the *Lactuca* plant.

<2> The method according to the above <1>, wherein the *Lactuca* plant seed is a first filial generation seed (F1 hybrid) of the *Lactuca* plant.

<3> The method according to the above <1> or <2>, wherein the *Lactuca* plant is lettuce (*Lactuca sativa*).

<4> The method according to any one of the above <1> to <3>, wherein the *Megachile* bee is an alfalfa leaf cutting bee.

<5> The method according to any one of the above <1> to <4>, wherein the minor nectar plant has a flowering habit in which a flower of the minor nectar plant is opened even when a flower of the *Lactuca* plant is closed.

<6> The method according to any one of the above <1> to <5>, wherein the minor nectar plant used is one or more genera selected from the group consisting of an *Anthemis* plant, a *Coriandrum* plant, a *Hyssopus* plant, a *Monarda* plant, a *Nepeta* plant, a *Pentapetes* plant, a *Salvia* plant, a *Erigeron* plant, a *Foeniculum* plant, a *Melampodium* plant, a *Portulaca* plant, and a *Torenia* plant.

<7> The method according to any one of the above <1> to <6>, wherein the minor nectar plant used is one or more species selected from the group consisting of dyers chamomile (*Anthemis tinctoria*), coriander (*Coriandrum sativum*), hyssop (*Hyssopus officinalis*), bergamot (*Monarda didyma*), catnip (*Nepeta cataria*), midday flower (*Pentapetes phoenicea*), blue sage (*Salvia azurea*), mexican fleabane (*Erigeron karvinskianus*), fennel (*Foeniculum vulgare*), gold medallion flower (*Melampodium paludosum*), moss-rose Purslane (*Portulaca grandiflora*), and bluewings (*Torenia fournieri*).

<8> The method according to any one of the above <1> to <7>, wherein the minor nectar plant used is one or more species selected from the group consisting of Mexican fleabane, fennel, gold medallion flower, moss-rose purslane, and bluewings.

<9> The method according to any one of the above <1> to <8>, wherein the minor nectar plant used is one or two species selected from the group consisting of gold medallion flower and bluewings.

<10> The method according to any one of the above <1> to <9>, wherein as the minor nectar plant used is the gold medallion flower.

<11> The method according to any one of the above <1> to <10>, wherein the pollen parent *Lactuca* plant is a male fertile line and the seed parent *Lactuca* plant is a male sterile line.

<12> A method of crossing a *Lactuca* plant using a *Megachile* bee as pollination means, wherein
the minor nectar plant used is preferable to the *Megachile* bee for flower visiting and is a plant species in which the preference in flower visiting equivalent to or less than that of the *Lactuca* plant.

<13> The method according to the above <12>, wherein a crossing of the *Lactuca* plant is for obtaining (F1) hybrids of a first filial generation of the *Lactuca* plant.

<14> The method according to the above <12> or <13>, wherein the *Lactuca* plant is lettuce (*Lactuca sativa*).

<15> The method according to any one of the above <12> to <14>, wherein the *Megachile* bee is an alfalfa leaf cutting bee.

<16> The method according to any one of the above <12> to <15>, wherein the minor nectar plant has a flowering habit in which a flower of the minor nectar plant is opened when a flower of the *Lactuca* plant is closed.

Effects of the Invention

According to the present invention, the *Lactuca* plant seed, which had been difficult to efficiently produce by a pollinating insect can now be more efficiently produced by producing the minor nectar plant in the seed production field of the *Lactuca* plant and using the *Megachile* bee as the pollination means as compared to the related art. In addition, the method of the present invention can significantly reduce the cost and labor for producing the *Lactuca* plant seed.

EMBODIMENTS OF THE INVENTION

The embodiments of the invention will be described below in detail.

As described above, a method of producing a *Lactuca* plant seed according to the present invention includes using a *Megachile* bee as pollination means, and providing the *Megachile* bee as a minor nectar plant to have preference in flower visiting, in addition to a pollen parent *Lactuca* plant and a seed parent *Lactuca* plant and to perform a crossing of a *Lactuca* plant using plant species which the *Megachile* bee prefers equivally to or less than that of the *Lactuca* plant.

In the present invention, a *Lactuca* plant seed is produced. Here, a seed production means of producing a seed by crossing a *Lactuca* plant serving as a pollen parent and a *Lactuca* plant serving as a seed parent, that is, transferring a pollen of the pollen parent to a seed parent and producing a seed obtained by cultivating the seed parent.

Here, examples of the *Lactuca* plant include lettuce (*Lactuca sativa*), *Lactuca serriola*, *L. aculeate*, *L. scarioloides*, *L. azerbaijanica*, *L. georgica*, *L. dregeana*, *L. altaica*, *L. saligna*, *L. virosa*, *L. tatarica*, *L. indica*, *L. debilis*, or the like. In addition, the *Lactuca* plant may also include hybrids by a cell fusion of the lettuce (*Lactuca sativa*) with the *Lactuca* plant species described above other than the lettuce or hybrids by interspecific and intergeneric hybridization. Preferably, the *Lactuca* plant is one or more selected from the group of species listed above, and more preferably lettuce (*Lactuca sativa*).

In the method of the present invention, a flower visiting insect is used as pollination means for transporting a pollen from a pollen parent plant and pollinating a seed parent plant. A flower visiting insect, for example a *Megachile* bee, which is known to visit flowers of the *Lactuca* plant, is used. The *Megachile* bee is not particularly limited, but specifically, examples thereof include alfalfa leaf cutting bee (*Megachile* rotundata), *M. latimanus* (Reference Document 5), *M. brevis* (Reference Document 6), *M. montivaga* (Reference Document 7), *M. onobrychidis* (Reference Document 8), *M. dentitarsus* (Reference Document 9), *M. relativa* (Reference Document 10). These may be used alone or in combination of two or more. The *Megachile* bee is used as the flower visiting insect in the present invention and is preferable because it is readily available on the market.

The *Lactuca* plant seed to be produced in the present invention is preferably a first filial generation seed (F1 hybrid). Here, the first filial generation (F1) refers to a first generation offspring generated by hybridization between parents having certain allelomorphs in homo.

In the present invention, the seed parent is a parent line of the seed produced by the method of the present invention, and refers to a parent plant which is treated (such as washing away pollen with water) or produced (that is, produced to have male sterility) so as not to be pollinated by pollen having its own fertility. When the seed produced in the present invention is the F1 hybrid, the seed parent is preferably a line (male sterile line) which is produced such that fertile pollen cannot be formed. Specifically, for example, a line having male sterile cytoplasm is used as a mother plant and a non-recurrent parent, a target line which is confirmed to have no fertility recovery genetic factor is utilized as a recurrent parent. Then hybridization is performed and the cytoplasm of the target line is substituted with the male sterile cytoplasm, thereby making it possible to impart male sterility to the target line and obtain a seed parent line.

Further, in the present invention, the "seed parent *Lactuca* plant" means the *Lactuca* plant which becomes a seed parent. The seed parent *Lactuca* plant is preferably a male sterile line, more preferably a cytoplasm male sterile (CMS) line. An example of such a CMS line is described in Patent Document 1.

In the present invention, the pollen parent is a parent line of the seeds produced by the method of the present invention and refers to a line which supplies pollen. When the seeds produced in the present invention are F1 hybrids, the pollen parent is the male fertile line.

Further, in the present invention, the "pollen parent *Lactuca* plant" means the *Lactuca* plant which becomes the pollen parent. The pollen parent *Lactuca* plant is preferably the male fertile line.

Usually, in the seed production field, the pollen parent (preferably a male fertile line) and the seed parent (preferably a male sterile line) are preferably planted in a 1:1 ratio of alternating rows. This could differ depending on the ratio of the pollen parent and the seed parent needed in order to have uniform pollination of the pollen parent.

In the present invention, in addition to the pollen parent plant and the seed parent plant, the minor nectar plant is used.

The flowers of the *Lactuca* plant, including those of lettuce, have a flowering habit in which flowers open early in the morning and close after several hours. For this reason, the minor nectar plant is used in the present invention to prevent pollinator bees from starving due to lack of a nectar source when the flowers of the lettuce are closed. The minor nectar plant is prepared around a nest box of bees or around the pollen parent and/or seed parent *Lactuca* plant and is used as a nectar source.

For this reason, in the present invention, the minor nectar plant is a plant species in which the *Megachile* bee will flower visit and prefers to visit equally as much or less than that of the *Lactuca* plant. Even if the preference of the minor nectar plant is equivalent to that of the *Lactuca* plant, if, when the flowers are opened, the *Lactuca* plant could be a nectar source, it is possible to effectively produce the *Lactuca* plant seed using the *Megachile* bee. The method, later described in Example 1, is an example that can be utilized to confirm whether the flower visiting preference by bees is equivalent to or less than that of the *Lactuca* plant. Preferably, the minor nectar plant is a plant species preferred by the alfalfa leaf cutting bee and whose preference in flower visiting is equivalent to or less than that of lettuce.

More preferably, the minor nectar plant is a plant species preferred by the *Megachile* bee and which the preference in flower visiting is less than that of the *Lactuca* plant, and more preferably a plant species preferred by the alfalfa leaf cutting bee and which the preference in flower visiting is less than that of lettuce.

Ideally, the plant species chosen for the minor nectar plant, in addition to the above-mentioned preference in flower visiting, would preferably have a flowering habit opposite to that of the lettuce. Specifically, the plant species chosen for the minor nectar plant preferably has the excellent flowering sustainability as later described in Example 1. In addition, the plant species chosen for the minor nectar plant is preferably one that has excellent heat tolerance. The heat tolerance mentioned herein can be evaluated, for example, by the method later described in Example 1.

In the present invention, plants suitable to be the minor nectar plant are not particularly limited, but an example thereof includes an *Anthemis* plant, a *Coriandrum* plant, a *Hyssopus* plant, a *Monarda* plant, a *Nepeta* plant, a *Pentapetes* plant, a *Salvia* plant, a *Erigeron* plant, a *Foeniculum* plant, a *Melampodium* plant, a *Portulaca* plant, and a *Torenia* plant. According to one preferred embodiment of the present invention, one or more species selected from plants of the genera listed above can be used as the minor nectar plant. In the present invention, the most preferable plants of the listed genera are those having a flowering habit opposite to that of lettuce, in addition to the above-mentioned preference in flower visiting in the plants of these genera.

According to a further preferred embodiment of the present invention, from the plants which are suitable for the minor nectar plant, one or more selected from the *Erigeron* plant, the *Foeniculum* plant, the *Melampodium* plant, the *Portulaca* plant, and the *Torenia* plant can be used, more preferably, one or two species selected from the group consisting of the *Melampodium* plant and the *Torenia* plant is used, and most preferably, the *Melampodium* plant is used.

According to the preferred aspect of the present invention, examples of the plant species which are suitable for the minor nectar plant include dyers chamomile (*Anthemis tinctoria*), coriander (*Coriandrum sativum*), hyssop (*Hyssopus officinalis*), bergamot (*Monarda didyma*), catnip (*Nepeta cataria*), midday flower (*Pentapetes phoenicea*), blue sage (*Salvia azurea*), Mexican fleabane (*Erigeron karvinskianus*), fennel (*Foeniculum vulgare*), gold medallion flower (*Melampodium paludosum*), moss-rose Purslane (*Portulaca grandiflora*), and bluewings (*Torenia fournieri*). According to one preferred embodiment of the present invention, one or more species selected from the listed plant species can be used as the minor nectar plant.

According to a more preferred embodiment of the present invention, in the method of the present invention, one or more species selected from the group consisting of Mexican fleabane, fennel, gold medallion flower, moss-rose purslane, and bluewings are used as the minor nectar plant. More preferably, one or two species selected from the group consisting of gold medallion flower and bluewings are used as the minor nectar plant, and particularly preferably, gold medallion flower is used.

It is preferable to appropriately adjust the planting time of the minor nectar plant to match the flowering time of the *Lactuca* plant according to the flowering property. For example, the gold medallion flower and the bluewings flower bloom about 1.5 months after being sown in the spring. Both plants have a continuous flowering property and will continue to bloom until late autumn. In this case, the plants are not required to match the flowering time of the *Lactuca* plant, but work can be performed efficiently by sowing and planting the minor nectar plant simultaneously with the *Lactuca* plant. Therefore, it is preferable to sow and plant the gold medallion flower and the bluewings simultaneously with the *Lactuca* plant. On the other hand, when a plant species having low continuous flowering property is used as the minor nectar plant, it is necessary to appropriately adjust the planting time to match the flowering time of the *Lactuca* plant according to the flowering property.

The ratio of planting number of the minor nectar plant and the *Lactuca* plant is not particularly limited, but can be optionally adjusted according to the type of minor nectar plants and the cultivation environment. For example, the ratio of planting number is in the range of the *Lactuca* plant:minor nectar plant=2:1 to 20:1, preferably, the range of the *Lactuca* plant:minor nectar plant=2:1 to 4:1, and more preferably, is in the range of the *Lactuca* plant:minor nectar plant=about 5:2.

It is preferable that the planting location of the minor nectar plant is around a hive which is the pollination means, but the planting location of the minor nectar plant may be distributed in the field or around the field.

The active flower visiting activity by the *Megachile* bee (for example, alfalfa leaf cutting bee) usually requires a temperature of 25° C. or higher. For this reason, it is preferable to cultivate the *Lactuca* plant used for the seed production in the environment that the temperature of the flowering time is 25° C. or higher during the day.

The *Megachile* bee (for example, alfalfa leaf cutting bee) has homing ability and therefore can be used even in the open field and the like, in addition to a net cage of the closed facility. That is, the present invention can be practiced even in the field facility of any of the open one or the closed one. Therefore, in an environment where a *Lactuca* plant which is likely to cause unintentional and undesirable hybridization does not exist around, the method is preferably used in the open field where the production cost is low.

As a method of incubating and releasing a *Megachile* bee, and the like, the conventional methods known to those skilled in the art can be used. For example, Reference Document 3 can be referenced as appropriate. In addition, the method of incubating and releasing alfalfa leaf cutting bee and the like can be practiced according to the conventional seed production method of alfalfa.

When the *Megachile* bee (for example, alfalfa leaf cutting bee) is used for the seed production of the *Lactuca* plant, it is preferable to release the *Megachile* bee at an interval of 1 to 2 weeks.

In addition, the preferred release density of the *Megachile* bee (for example, alfalfa leaf cutting bee) is preferably 5 or more per release per plant, but the release density depends on the cultivation environment as well as the difference in the line of the *Lactuca* plant used, and therefore it is preferable to make appropriate adjustments in consideration of cost as well.

The release of the *Megachile* bee (for example, alfalfa leaf cutting bee) is preferably practiced in the evening of the previous day or in the early morning before sunrise. Since the pollen parent of the *Lactuca* plant stops flowering when seed is set, it is preferable to force the pollen parent to continuously flower and appropriately cut back the pollen parent so that pollen can be supplied for a long period of time.

REFERENCE DOCUMENTS

[Reference Document 1] W. P. KEMP et al., "Development and Emergence of the Alfalfa Pollinator *Megachile rotundata* (Hymenoptera: Megachilidae)", Annals of the Entomological Society of America, 93(4):904-911(2000)

[Reference Document 2] Eric Mader et al., "Managing Alternative Pollinators: A Handbook for Beekeepers, Growers, and Conservationists", SARE Handbook 11 (2010), p10

[Reference Document 3] Matsuka Mitsuo, "Insect Utilization Science Series 7 Pollinator", First Edition, Science House, Inc., February 1996, p. 97-112

[Reference Document 4] Dave Goulson, "EFFECTS OF INTRODUCED BEES ON NATIVE ECOSYSTEMS", Annu. Rev. Ecol. Evol. Syst. 34:1-26 (2003), p6,

[Reference Document 5] "American Museum of Natural History, Bee Specimen Record database", ID_parent AMNH_BEE00026543, [online], American Museum of Natural History, [Search on Nov. 6, 2017], Internet (http://www.discoverlife.org/mp/201?id=AMNH_BEE00026543;AMNH_BEE00026532; AMNH_BEE00026530;AMNH_BEE00107964)

[Reference Document 6] "American Museum of Natural History, Bee Specimen Record database", ID_parent AMNH_BEE00015546, [online], American Museum of Natural History, [Search on Nov. 6, 2017], Internet (http://www.discoverlife.org/mp/201?id=AMNH_BEE000-15546;AMNH_BEE00015755)

[Reference Document 7] John Pickering, "DISCOVER LIFE", [online], [Search on Nov. 6, 2017], Internet (http://www.discoverlife.org/mp/20q)

[Reference Document 8] "American Museum of Natural History, Bee Specimen Record database", ID_parent AMNH_BEE00220721, [online], American Museum of Natural History, [Search on Nov. 6, 2017], Internet (http://www.discoverlife.org/mp/201?id=AMNH_BEE00220721; AMNH_BEE00015741)

[Reference Document 9] "Bee Biology and Lineatics Laboratory database", ID_parent BBSL200815, [online], Bee Biology and Lineatics Laboratory, [Search on Nov. 6, 2017], Internet (http://www.discoverlife.org/mp/201?id=BBSL200815)

[Reference Document 10] "American Museum of Natural History, Bee Specimen Record database", ID_parent AMNH_BEE00107046, [online], American Museum of Natural History, [Search on Nov. 6, 2017], Internet (http://www.discoverlife.org/mp/201?id=AMNH_BEE0010-7046;AM- NH_BEE00107116)

EXAMPLES

Hereinafter, the present invention will be described in more detail with reference to the following examples, but the present invention is not limited by these examples at all.

Example 1: Examination of Minor Nectar Plant

In the present invention, important characteristics as a minor nectar plant are that a *Megachile* bee has preference in flower visiting and the preference in flower visiting is equivalent to or lower than that of the *Lactuca* plant. Therefore, plant species having such characteristics were selected and examined.

In a test, the alfalfa leaf cutting bee was used as the *Megachile* bee, and lettuce was used as the *Lactuca* plant.

A primary seed production area of lettuce is the San Joaquin Valley in California, USA which is a hot and dry inland climate. In the seed production in San Joaquin Valley, a minor nectar plant needs to have heat tolerance because a maximum temperature at which the lettuce flowers and sets seed can be 40° C. or higher. Generally, an optimum growth temperature for lettuce is around 20° C. However, under the high temperature environment, for the purpose of producing seeds free of virus, seeds are produced in high temperature environment because aphid which transmit this virus to the lettuce cannot survive. The lettuce has low heat tolerance in the presence of head-formed leaves, but the lettuce has high heat tolerance by appropriately removing the head-formed leaves and shows that the lettuce has extremely high heat tolerance when it changes to the reproductive phase.

The flowering period of the lettuce ranges from one to two months. Since it is necessary for the minor nectar plant to flower during that period, the minor nectar plant preferably is a plant species having a continuous flowering property. In addition, if the cultivation area of the minor nectar plant is wide, since the cultivation area of the lettuce is limited, and the yield of seed production of the lettuce per unit area is decreased, multifloral plant species having many flowers is preferable.

In order to find plant species that are candidates for a minor nectar plant in the seed production of F1 hybrids of lettuce, 57 plant species possessing relatively high heat tolerance and flowerings in the summer season were selected, and their characteristics were evaluated.

The lettuce and other plant species which are candidates for the minor nectar source started to be sown and produced in early May using an unheated glass greenhouse in Kakegawa City, Shizuoka Prefecture.

Each plant species was planted in a plastic pot having a diameter of 15 cm as one or two plants at a suitable time. Each plant was cultivated at a temperature of 35° C. which was higher than usual cultivation temperature in order to select the plant species that could withstand the high temperature of the main seed production area. Actually, on a clear day during July to August, the temperature in the greenhouse often exceeded 40° C. and the temperature was considerably high. Since the cultivation of the lettuce depends on the actual method of seed production, an operation of removing head-formed leaves removal was performed until bolting.

Therefore, the following test was performed to evaluate the flower foraging preference of an alfalfa leaf cutting bee.

Specifically, the time from a start of flower visiting of the alfalfa leaf cutting bee to the time of flower visiting of another plant species was investigated. This was a criterion for the selection of the optimal minor nectar plant species.

Evaluation of Preference in Flower Visiting

Fifty-seven kinds of plants selected were cultivated in the same greenhouse and placed on a cultivation shelf at intervals of 30 cm. A pot of plant species to be investigated was transferred to a separate cultivation shelf at a distance of 1 meter and the flower visiting behavior of alfalfa leaf cutting bee was investigated. About 300 alfalfa leaf cutting bees were released in a glass greenhouse, and flower visiting was investigated five times per plant species to calculate an average flower visiting time.

The preference in flower visiting was evaluated by dividing the average flower visiting time from the start of the flower visiting to the time for flower visiting to other plant species into the following five-stage rating.

Rating-average flower visiting time
1: No flower visiting,
2: 1 second or more and less than 15 seconds,
3: 15 seconds or more and less than 30 seconds,
4: 30 seconds or more and less than 60 seconds,
5: 60 seconds or more The results are shown in Table 1.

The "-" in the table indicates that no flowering of the plant species was observed at the flowering time of the lettuce, or no flowering was observed because the plant species dies in the middle of cultivation.

As a result of observing the behavior of the alfalfa leaf cutting bee at the time of flower visiting, it was observed that in plant species having high preference in flower visiting, the time from the start of flower visiting to transfer to another plant species is long and the alfalfa leaf cutting bee has the tendency to visit the same plant species repeatedly.

From the evaluation results of the preference in flower visiting in Table 1, it was confirmed that the alfalfa leaf cutting bee visits 30 out of 33 plant species that reached flowering and has the preference in flower visiting to a wide range of plant species.

As a result, a rating of the preference in flower visiting of the lettuce was 3.

The seven plant species considered to have preference in flower visiting by the alfalfa leaf cutting bee equivalent to that of lettuce were dyers chamomile, coriander, hyssop, bergamot, catnip, midday flower, and blue sage, which have a flower visiting rating of 3.

The five plant species considered to have preference in flower visiting by the alfalfa leaf cutting bee lower than that of lettuce were Mexican fleabane, fennel, gold medallion flower, moss-rose purslane, and bluewings, which have a flower visiting rating of 2.

Evaluation of Heat Tolerance

In addition to the above-mentioned evaluation of preference in flower visiting, heat tolerance was evaluated.

The heat tolerance test was evaluated by performing cultivation in a greenhouse set at 35° C. and visually observing growth status of each plant species at the flowering time of lettuce. Specifically, plant species which have died were rated 1 (plant death), plant species which have a weak growth as compared to a normal growth under proper-temperature environment were rated 2 (weak heat tolerance), and plant species which have an equivalent growth as compared to a normal growth under the proper-temperature environment were rated 3 (strong heat tolerance).

The results are shown in Table 1.

In this test, since plant species having relatively high heat tolerance and flowering during the summer season were selected as candidates in extremely high temperature environment, as shown in the evaluation results of the heat tolerance shown in Table 1, 21 species of plants died (a rating of heat tolerance is 1), and 20 species of plants became growth failure due to high temperature (a rating of heat tolerance is 2).

In this test, the heat tolerance rating of the lettuce was 3, and no growth failure was observed. The bolted lettuce had extremely high heat tolerance, such that to be considered that a minor nectar plant is also required to have the same heat tolerance.

Therefore, considering the heat tolerance together with the results of the flowering evaluation, Mexican fleabane, fennel, and moss-rose purslane have somewhat less heat-tolerance, such that it was considered that gold medallion flower and bluewings are a more promising candidate as the minor nectar plant.

Evaluation of Flowering Sustainability

An evaluation test for flowering sustainability were also conducted together with an evaluation test for preference in flower visiting described above.

Specifically, the flowering sustainability was evaluated by dividing a period from a start of flowering to an end of flowering into the following five stages.

Rating-Period from start of flowering to end of flowering
1: Less than 2 weeks,
2: 2 weeks or more and less than 1 month,
3: 1 month or more and less than 2 months,
4: 2 months or more and less than 3 months,
5: 3 months or more The results are shown in Table 1.

In the evaluation of the flowering sustainability, it could be confirmed that lettuce started to flower from the middle of August, whereas gold medallion flower started to flower from the end of June, bluewings started to flower from the beginning of July, and both species continuously flowered until the harvest of F1 hybrids of lettuce were completed, and the flowering sustainability has no problem.

From the above results, Mexican fleabane, fennel, and moss-rose purslane could be used as the minor nectar plant if seed production areas were not under high temperature environment, but it was concluded that gold medallion flower and bluewings were more promising as the minor nectar plant under high temperature environments like the current major seed production areas for lettuce.

TABLE 1A

Table 1
Evaluation on characteristics of minor nectar plant

| No. | Species name | Botanical name | Preference on flower visiting (1-5) | Heat tolerance (1-3) | Flowering sustainability (1-5) |
| --- | --- | --- | --- | --- | --- |
| 1 | Lettuce | *Lactuca sativa* | 3 | 3 | 3 |
| 2 | Sneeze-wort | *Achillea ptarmica* | 1 | 3 | 3 |
| 3 | Tall anemone | *Anemone virginiana* | — | 1 | — |
| 4 | Dyers chamomile | *Anthemis tinctoria* | 3 | 2 | 3 |
| 5 | Borage | *Borago officinallis* | 5 | 3 | 3 |
| 6 | Lesser calamint | *Calamintha nepetoides* | 4 | 3 | 2 |
| 7 | China Aster | *Callistephus chinensis* | 5 | 2 | 2 |
| 8 | Rampion bellflower | *Campanula Rapunciloides* | — | 1 | — |
| 9 | Plumed cockscomb | *Celosia argentea* | 5 | 2 | 5 |
| 10 | Red valerian | *Centranthus ruber* | — | 1 | — |
| 11 | Spider flower | *Cleome hassleriana* | — | 1 | — |
| 12 | Silver bush | *Convolvulus cneorum* | — | 1 | — |
| 13 | Coriander | *Coriandrum sativum* | 3 | 2 | 2 |
| 14 | Livingstone Daisy | *Dorotheanthus bellidiformis* | — | 1 | — |
| 15 | Eastern purple-coneflower | *Echinacea purpurea* | 4 | 3 | 3 |
| 16 | Mexican fleabane | *Erigeron karvinskianus* | 2 | 2 | 2 |
| 17 | Mist flowers | *Eupatorium coelestinum* | — | 1 | — |
| 18 | Buckwheat | *Fagopyrum esculentum* | 5 | 2 | 4 |
| 19 | Fennel | *Foeniculum vulgare* | 2 | 2 | 3 |
| 20 | White gaura | *Gaura lindheimeri* | 4 | 2 | 2 |
| 21 | Globe amaranth | *Gomphrena globosa* | 4 | 2 | 5 |
| 22 | Sunflower | *Helianthus annuus* | 5 | 3 | 1 |
| 23 | St. John's wort | *Hypericum perforatum* | — | 1 | — |
| 24 | Hyssop | *Hyssopus officinalis* | 3 | 2 | 3 |
| 25 | Evergreen candytuft | *Iberis sempervirens* | 5 | 1 | 2 |
| 26 | Trailing ice plant | *Lampranthus spectabilis* | — | 1 | — |
| 27 | Tree marrow | *Lavatera thuringiaca* | — | 2 | 2 |
| 28 | Spurred snapdragon | *Linaria purpurea* | — | 2 | — |
| 29 | Carpet grass | *Lippia repens* | — | 3 | — |
| 30 | Ragged Robin | *Lychnis flos-cuculi* | — | 1 | — |
| 31 | Alfalfa | *Medicago sativa* | 4 | 3 | 2 |
| 32 | Gold medallion flower | *Melampodium paludosum* | 2 | 3 | 5 |

TABLE 1A-continued

Table 1
Evaluation on characteristics of minor nectar plant

| No. | Species name | Botanical name | Preference on flower visiting (1-5) | Heat tolerance (1-3) | Flowering sustainability (1-5) |
|---|---|---|---|---|---|
| 33 | Pennyroyal flea mint. | *Mentha pulegium* | 4 | 2 | 4 |
| 34 | Bergamot | *Monarda didyma* | 3 | 2 | 2 |
| 35 | Cat mint | *Nepeta × faassenii* | 4 | 2 | 4 |
| 36 | Catnip | *Nepeta cataria* | 3 | 3 | 5 |
| 37 | Cup flower | *Nierembergia caerulea* | 1 | 2 | 4 |
| 38 | Marjoram | *Origanum majorana* | 5 | 3 | 4 |

TABLE 1B

| No. | Species name | Botanical name | Preference on flower visiting (1-5) | Heat tolerance (1-3) | Flowering sustainability (1-5) |
|---|---|---|---|---|---|
| 39 | Southern star | *Oxypetalum coeruleum* | — | 1 | — |
| 40 | Beardtongue | *Penstamon digitalis* | — | 1 | — |
| 41 | Midday flower | *Pentapetes phoenicea* | 3 | 2 | 2 |
| 42 | Creeping phlox | *Phlox stolonifera* | — | 1 | — |
| 43 | Caucasian crossword | *Phuopsis stylosa* | — | 1 | — |
| 44 | Moss-rose Purslane | *Portulaca grandiflora* | 2 | 2 | 5 |
| 45 | Alpine cinquefoil | *Potentilla crantzii* | — | 1 | — |
| 46 | Blue sage | *Salvia azurea* | 3 | 2 | 2 |
| 47 | Cherry sage | *Salvia microphylla* | — | 1 | — |
| 48 | May night sage | *Salvia nemorosa* | 4 | 3 | 2 |
| 49 | Pincushion Flower | *Scabiosa columbaria* | — | 1 | — |
| 50 | Marigold | *Tagetes patula* | 1 | 3 | 5 |
| 51 | White Tansy | *Tanacetum niveum* | — | 1 | — |
| 52 | Common thyme | *Thymus vulgaris* | 4 | 2 | 3 |
| 53 | Bluewings | *Torenia fournieri* | 2 | 3 | 5 |
| 54 | White Clover | *Trifolium repens* | — | 3 | — |
| 55 | Purpletop vervain | *Verbena bonariensis* | 4 | 3 | 3 |
| 56 | Blue vervain | *Verbena hastata* | — | 1 | — |
| 57 | Long-leaf speedwell | *Veronica longifolia* | — | 1 | — |

Example 2: Investigation of Starvation Resistance of Alfalfa Leaf Cutting Bee

Since lettuce have a special flowering habit in which they flower early in the morning and are closed after several hours, when alfalfa leaf cutting bee is released in the seed production field of the lettuce, a nectar source is lost after the flowers of the lettuce close. The alfalfa leaf cutting bee has the property of actively continuing the foraging activity if the temperature is 25° C. or higher and the weather is clear.

Therefore, the effect of the loss of the nectar source, that is, the starvation resistance of alfalfa leaf cutting bee was evaluated.

The test was performed as follows.

Eight pots of the lettuce which is cultivated in pots No. 10, respectively, (about 30 cm in diameter) and is at the flowering season were placed in the glass greenhouse in Kakegawa City, Shizuoka Prefecture, and only 4 gold medallion flower pots were placed in one glass greenhouse. A glass greenhouse in which gold medallion flower is not placed was set as test area A, and a glass greenhouse in which gold medallion flower is placed was set as test area B.

About 50 alfalfa leaf cutting bees were introduced into each glass greenhouse at the evening of the day before the investigation, and the number of insects visiting flowers of alfalfa leaf cutting bee was investigated.

The investigation of the number of insects visiting flowers was done in the morning at the time of the flowering the lettuce, and the number of alfalfa leaf cutting bee visiting flowers of 8 pots of lettuce was visually counted. This was repeated three times at intervals of about 5 minutes.

As the number of insects visiting flowers, an average of flower visiting insects of alfalfa leaf cutting bee visiting lettuce was obtained.

The results are shown in Table 2.

TABLE 2

Table 2: Investigation on starvation resistance of Alfalfa leaf cutting bee

| Test area | Minor nectar plant | Number of flower visiting insects | | | | |
|---|---|---|---|---|---|---|
| | | First day | Second day | Third day | Fourth day | Fifth day |
| A | None | 28.0 | 3.7 | 2.0 | 0.0 | 0.0 |
| B | Gold medallion flower | 25.7 | 23.0 | 18.0 | 14.7 | 19.3 |

During the test period, the flowers of the lettuce are opened around 7 am and closed around 9 am.

The number of insects visiting the flowers of the alfalfa leaf cutting bee in the morning on the first day (the day after alfalfa leaf cutting bee was introduced) was 28.0 in the test area A and 25.7 in the test area B, which was not a significant difference.

On the second day, the number of insects visiting the flowers of the alfalfa leaf cutting bee was 3.7 in the test area A and 23.0 in the test area B, which was a significant difference.

In the test area A, most of alfalfa leaf cutting bee consumed their physical strength and starved to death or lost their flower visiting ability because nectar sources were lost from the greenhouse after the flowers of the lettuce were closed. In the test area A, the number of alfalfa leaf cutting bee was 2 on the third day, and no flower visiting was observed after the fourth day, and all alfalfa leaf cutting bee starved to death.

In the test area B, although the number of insects visiting flowers tends to be decreased, on the fifth day, the flower visiting of about 20 alfalfa leaf cutting bees was observed, and 20 alfalfa leaf cutting bees were settled in a glass greenhouse and stable pollination activity was observed.

During the test period, because of the good weather, the activity of the alfalfa leaf cutting bee started at around 7 am and continued around 4 pm. That is, it was considered that the alfalfa leaf cutting bee lost a nectar source in the test area A for about 7 hours from 9 am to 4 pm.

From the above results, it was considered that the alfalfa leaf cutting bee consumed its physical strength during the 7 hours when the nectar source was lost and starved to death or lost the flower visiting reserve power, because the flowers of the lettuce were closed and foraging activity continued in an environment where there was no nectar source. Therefore, as described in Patent Document 5 (paragraph 0048), cutting off the flowers of the alfalfa in order to concentrate the alfalfa leaf cutting bee on the lettuce was considered to be an important factor of decreasing the pollination from the next day of the alfalfa leaf cutting bee.

On the other hand, it was confirmed that when the minor nectar plant was present, even after the flowers of the lettuce were closed, the normal foraging activity using the minor nectar source of the alfalfa leaf cutting bee was observed until homing around 4 pm. The starvation due to the loss of the nectar source could be prevented, and the pollination activity from the next day could be continued.

Example 3: Investigation of Flower Visiting Frequency by Difference in Plant Species The foraging activity of the alfalfa leaf cutting bee, that is, the flower visiting frequency were investigated when lettuce, gold medallion flower, and bluewings were placed in the same glass greenhouse.

The test was performed as follows.

Eight pots of lettuce, 2 pots of gold medallion flower, and 2 pots of bluewings, which were each cultivated in No. 10 pot and at the time of flowering season were placed in a glass greenhouse in Kakegawa City, Shizuoka Prefecture.

About 100 of alfalfa leaf cutting bee were introduced. The temperature setting of the greenhouse was 35° C., which is close to the temperature of the main seed production site.

In the test, the number (VN) of alfalfa leaf cutting bee which visited flowers and the occupancy rate (VS) of alfalfa leaf cutting bee which visited flowers were determined.

Figure 1:
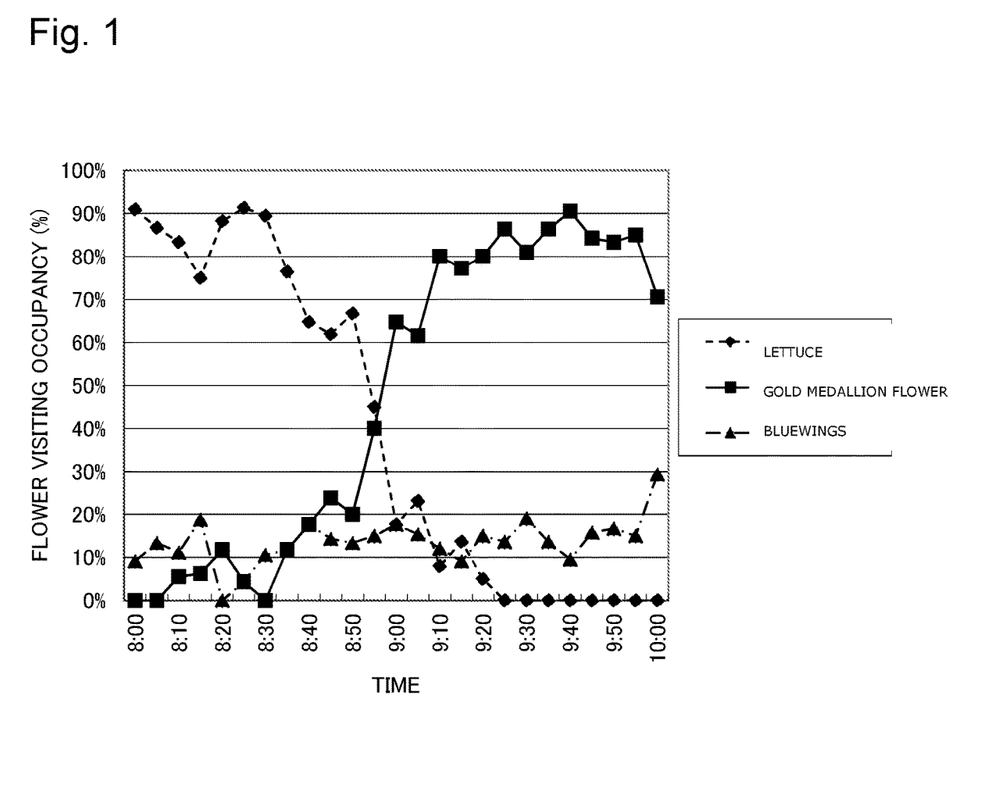
FIG. 1 is a graph showing investigation results on a frequency of flower visiting among different plant species in Example 3.

The results were shown in Table 3 and FIG. 1.

Table 3 shows the investigation results of the flower visiting frequency among different plant species, and the results are shown in FIG. 1 in a graph.

Table 3

TABLE 3

Investigation on flower visiting frequency between different plant species

| Time | Lettuce VN | Lettuce VS | Gold medallion flower VN | Gold medallion flower VS | Bluewings VN | Bluewings VS | Sum of flower visiting frequency of alfalfa leaf cutting bee |
|---|---|---|---|---|---|---|---|
| 8:00 | 10 | 91% | 0 | 0% | 1 | 9% | 11 |
| 8:05 | 13 | 67% | 0 | 0% | 2 | 13% | 15 |
| 8:10 | 15 | 63% | 1 | 6% | 2 | 11% | 18 |
| 8:15 | 12 | 75% | 1 | 6% | 3 | 19% | 16 |
| 8:20 | 15 | 68% | 2 | 12% | 0 | 0% | 17 |
| 8:25 | 21 | 91% | 1 | 4% | 1 | 4% | 23 |
| 8:30 | 17 | 89% | 0 | 0% | 2 | 11% | 19 |
| 8:35 | 13 | 76% | 2 | 12% | 2 | 12% | 17 |
| 8:40 | 11 | 65% | 3 | 18% | 3 | 18% | 17 |
| 8:45 | 13 | 62% | 5 | 24% | 3 | 14% | 21 |
| 8:50 | 10 | 67% | 3 | 20% | 2 | 13% | 15 |
| 8:55 | 9 | 45% | 8 | 40% | 3 | 15% | 20 |
| 9:00 | 3 | 18% | 11 | 65% | 3 | 18% | 17 |
| 9:05 | 3 | 23% | 8 | 62% | 2 | 15% | 13 |
| 9:10 | 2 | 8% | 20 | 80% | 3 | 12% | 25 |
| 9:15 | 3 | 14% | 17 | 77% | 2 | 9% | 22 |
| 9:20 | 1 | 5% | 16 | 80% | 3 | 15% | 20 |
| 9:25 | 0 | 0% | 19 | 66% | 3 | 14% | 22 |
| 9:30 | 0 | 0% | 17 | 61% | 4 | 19% | 21 |
| 9:35 | 0 | 0% | 19 | 66% | 3 | 14% | 22 |
| 9:40 | 0 | 0% | 19 | 90% | 2 | 10% | 21 |
| 9:45 | 0 | 0% | 16 | 64% | 3 | 16% | 19 |
| 9:50 | 0 | 0% | 15 | 83% | 3 | 17% | 18 |
| 9:55 | 0 | 0% | 17 | 85% | 3 | 15% | 20 |
| 10:00 | 0 | 0% | 12 | 71% | 5 | 29% | 17 |

VN: The number of alfalfa leaf cutting bees visiting flower
VS: Occupancy of alfalfa leaf cutting bee visiting flower The flowers of the lettuce started to open around 7 am.

The investigation of the foraging activity started from 8 am, and most of the alfalfa leaf cutting bee visited the flowers of the lettuce. The flowers of the lettuce started to close around 8:30 am.

The flower visiting frequency (that is, flower visiting occupancy (VS)) of the alfalfa leaf cutting bee to the gold medallion flower was gradually increased from around 8:35 am at which the flowers of the lettuce started to be closed, and the flower visiting frequency of the lettuce and the gold medallion flower were reversed at 8:55 am. At this time, most of the flowers of lettuce were in a closed state, and it was difficult for the alfalfa leaf cutting bee to forage on the lettuce. All flowers of the lettuce were completely closed at 9:25 am and most of the alfalfa leaf cutting bee visited the gold medallion flower. At this time, the flower visiting frequency to the bluewings was suppressed to 10% or less. The reason was that the preference in flower visiting of the alfalfa leaf cutting bee to the gold medallion flower was higher than that of the bluewings and lower than that of the lettuce.

From the above results, it was confirmed that the alfalfa leaf cutting bee intensively visits the flowers of the lettuce during the flowering of the lettuce and intensively visits the flowers of the gold medallion flower during the lettuce flower to be closed. Therefore, it was considered that the gold medallion flower is the optimum minor nectar plant in the seed production of the F1 hybrids of the lettuce. It was considered that the preference in flower visiting of the alfalfa leaf cutting bee becomes high in the order of the lettuce, the gold medallion flower, and the bluewings. From the results of this test, it could be confirmed that the preference in flower visiting of the alfalfa leaf cutting bee to the bluewings was lower than that of the *Lactuca sativa*, and showed that the bluewings can be used as the minor nectar plant when only the lettuce and the bluewings are placed alone.

Example 4: Seed Production Test of F1 Hybrid of Lettuce Using Gold Medallion Flower as Minor Nectar Plant In order to evaluate practicability of a method using gold medallion flower as a minor nectar plant in seed production of F1 hybrids of lettuce, a seed production test was practiced using a glass greenhouse.

"V lettuce" of a male fertile line was tested as a pollen parent, and "CMS V lettuce" of a cytoplasm male sterile line was tested as a seed parent.

The lettuce was sown in 72-hole plug trays on Feb. 10, 2016 in Kakegawa City, Shizuoka Prefecture, and was produced in an artificial growth chamber set at 20° C. and illuminated for 16 hours day length. Seedlings were transplanted to No. 3 (9 cm in diameter) pot on March 16 and continued to be produced in an unheated greenhouse. The plants were transplanted to No. 10 pots on April 11 and cultivated in a glass greenhouse set at 30° C. In addition, gold medallion flower and alfalfa plants, to be used as minor nectar plants, were sown, transplanted, planted and cultivated in the same environment and in the same method at the same time with lettuce.

Figure 2:
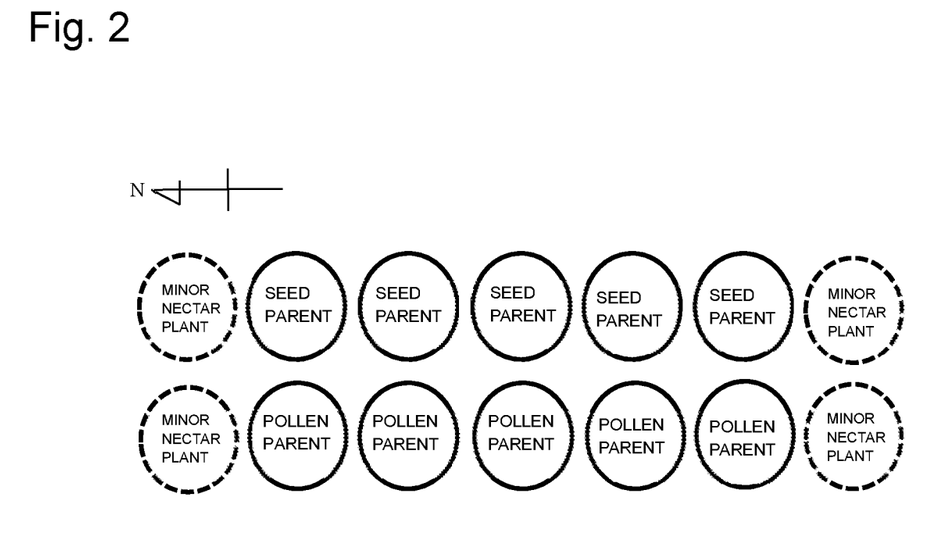
FIG. 2 is a diagram showing an arrangement of a seed parent, a pollen parent, and a minor nectar plant (alfalfa or gold medallion flower) (minor bee plant in the diagram) in a greenhouse in Example 4.

In order to compare the usefulness of the gold medallion flower and the alfalfa as the minor nectar plants, two greenhouses which were in the same environment in Kakegawa City, Shizuoka Prefecture were used. In each greenhouse, five plants of a pollen parent and 5 plants of a seed parent of lettuce were placed in a glass greenhouse as shown in FIG. 2. Four plants of the gold medallion flower and the alfalfa, respectively, were placed at positions of minor bee plants in FIG. 2 in their respective greenhouses.

However, since the alfalfa is deprived of energy to be set seeds and is temporarily paused to flower, the alfalfa needs to be pruned two weeks before the flowering of the lettuce is expected to flower so as to be synchronized with the flowering time of the lettuce.

The alfalfa leaf cutting bee was stored in a refrigerator at 4° C. before use, and leaf cells were transferred to an artificial growth chamber of 30° C. 23 days before release date and were subjected to incubation for emergence. The release was done three times at intervals of two weeks in the evening of June 28, July 14, and August 5. One time release quantity was set to be 200 ml (about 250 bees) as the capacity of leaf cells.

Since the plants of the male fertile line is paused to flower when setting seed, half of the pollen parents were pruned on June 27, and then the pollen parents were pruned by half every two weeks on July 11 and July 25, and the pollen parents were contrived to flower continuously.

After two months from flowering of a first flower, on August 25, seeds were harvested from every plant of seed parent. The harvested seeds were processed, and a seed weight was measured by an electronic balance for every plant of a seed parent.

The results are shown in Table 4.

TABLE 4

Table 4: Result of seed production of F1 seed of lettuce using alfalfa and gold medallion flower as minor nectar plant

| Test area | Minor nectar plant | Seed production amount per plant (g) | | | | | Average seed production amount per plant (g) |
| --- | --- | --- | --- | --- | --- | --- | --- |
| | | 1 | 2 | 3 | 4 | 5 | |
| C | Alfalfa | 4.6 | 7.1 | 4.3 | 7.3 | 4.2 | 5.5 |
| D | Gold medallion flower | 14.2 | 14.8 | 12.0 | 9.0 | 11.3 | 12.3 |

In test area C where the alfalfa was used as the minor nectar plant, the average seed production amount per plant was 5.5 g. In test area D where the *Melapodium paludosum* was used as the minor nectar plant, the average amount of seed production per plant was 12.3 g and 2.2 times as compared with the use of alfalfa.

When the alfalfa is used as the minor nectar plant, the alfalfa leaf cutting bee has a very high preference in flower visiting to the alfalfa as compared to lettuce, and even if the *Lactuca* flowers, since the flower visiting frequency to the alfalfa is high, it was considered that a pollination amount of the pollen of the lettuce from the pollen parent to the seed parent is reduced. On the other hand, when the *Melapodium paludosum* is used as the minor nectar plant, since the alfalfa leaf cutting bee has lower preference in flower visiting to the *Melapodium paludosum* as compared to the lettuce, it was considered that the flower visiting frequency of the alfalfa leaf cutting bee to the lettuce was high during the flowering of the lettuce and the pollination amount of the pollen of the lettuce from the pollen parent to the seed parent was large. It was considered that since the alfalfa leaf cutting bee visits the flowers of the gold medallion flower and is shifted to the foraging activity after the flowers of the lettuce are closed, the flowers of the gold medallion flower had the functions effectively as the minor nectar plant.

The result that the seed production amount of F1 hybrids of the lettuce is twice or more means that using the gold medallion flower as the minor nectar plant can reduce the production cost to half or less, which is considered that the utility value is very high. In addition, once the alfalfa has set seed, since the flowering is paused, it needs to be pruned to match the flowering time of the lettuce, but the gold medallion flower has a high continuous flowering property and therefore need not be pruned. Therefore, it was considered that the method of using gold medallion flower as a minor nectar plant has a great advantage in terms of labor reduction.

Example 5: Seed Production Test of F1 Hybrid of Lettuce Using Bluewings as Minor Nectar Plant In order to evaluate practicability of a method using bluewings as a minor nectar plant in seed production of Lettuce F1 hybrids, a separate seed production test was practiced using a glass greenhouse.

"V lettuce" of a male fertile line was tested as a pollen parent, and "CMS V lettuce" of a cytoplasm male sterile line was tested as a seed parent.

The lettuce was sown in 72-hole plug trays on Apr. 16, 2017 in Kakegawa City, Shizuoka Prefecture, and was produced in a unheated glass greenhouse set at 20° C.

Seedling was transplanted to No. 3 (9 cm in diameter) pots on May 8 and continued to be produced in a unheated glass greenhouse. The seedlings were transplanted in No. 10 pots on May 29, and cultivated in a glass greenhouse set at 30° C. In addition, the bluewings used as minor nectar plants were sown, transplanted, planted and cultivated in the same environment and in the same method at the same time with lettuce. In order to investigate the usefulness of the bluewings as the minor nectar plant, 5 plants of a pollen parent and 5 plants of a seed parent of the lettuce were placed in a glass greenhouse as shown in FIG. 3.

Figure 3:
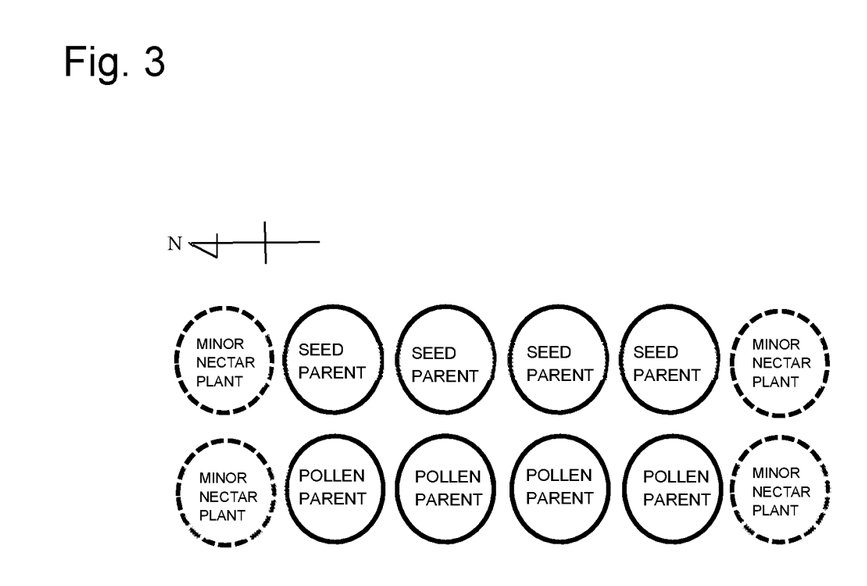
FIG. 3 is a diagram showing an arrangement of a seed parent, a pollen parent, and a minor nectar plant (*Torenia fournieri*) (minor bee plant in the diagram) in a greenhouse in Example 5.

Four plants of the bluewings were placed at a position of a nectar source plant in FIG. 3. Four pots of bluewings were tested for a total of eight plants of the seed parent and the pollen parent of the lettuce. The release of the alfalfa leaf cutting bee was done three times at intervals of two weeks in the evening of July 19, August 2, and August 16. One time release quantity was set to be 200 ml (about 250 bees) as the capacity of leaf cells. Since the lettuce of the male fertile line is paused to flower when setting seed, a half of the pollen parents were pruned on July 21, and then the pollen parents were pruned by half every two weeks on August 4 and August 18, and the pollen parents were contrived to flower continuously.

After two months from flowering of a first flower, on September 19, seeds were harvested from every plant of a seed parent. The harvested seeds were processed, and a seed weight was measured by an electronic balance for every plant of a seed parent.

The results are shown in Table 5.

TABLE 5

Table 5: Result of seed production of F1 seed of lettuce using bluewings as minor nectar plant

| Test area | Minor nectar plant | Seed production amount per plant (g) | | | | Average seed production amount per plant (g) |
|---|---|---|---|---|---|---|
| | | 1 | 2 | 3 | 4 | |
| E | Bluewings | 4.4 | 10.5 | 11.3 | 9.2 | 8.9 |

In test area E where the bluewings was used as the minor nectar plant, the average amount of seed production per plant was 8.9 g and 1.6 times as compared with the use of alfalfa of Example 4. It could be confirmed that compared to the case of using the gold medallion flower, the amount of seed production was reduced, but the bluewings could also be used as the minor nectar plant.

The invention claimed is:

1. A method of pollinating a *Lactuca* plant to produce a *Lactuca* plant seed, the method comprising the steps of:
   planting a pollen parent of the *Lactuca* plant;
   planting a seed parent of the *Lactuca* plant near the pollen parent of the *Lactuca* plant;
   selecting a minor nectar plant based on a preference in flower visiting by a *Megachile* bee, the preference of the *Megachile* bee for flowers of the selected minor nectar plant being equal to or less than a preference of the *Megachile* bee for flowers of the *Lactuca* plant;
   positioning the selected minor nectar plant at a location adjacent to each the pollen parent of the *Lactuca* plant and the seed parent of the *Lactuca* plant;
   providing the *Megachile* bee;
   and crossing the *Lactuca* plant by pollinating the pollen parent of the *Lactuca* plant and the seed parent of the *Lactuca* plant via the *Megachile* bee to produce the *Lactuca* plant seed,
   wherein the selected minor nectar plant Is at least one selected from the group consisting of an *Anthemis* plant, a *Coriandrum* plant, a *Hyssopus* plant, a *Monarda* plant, a *Nepeta* plant, a *Pentapetes* plant, a *Salvia* plant, an *Erigeron* plant, a *Foeniculum* plant, a *Melampodium* plant, a *Portulaca* plant, and a *Torenia* plant,
   the pollen parent of the *Lactuca* plant, the seed parent of the *Lactuca* plant, and the selected minor nectar plant grow simultaneously during production of the *Lactuca* plant seed, and
   the seed parent of the *Lactuca* plant is a male sterile line.

2. The method according to claim 1, wherein the *Lactuca* plant seed is a first filial generation seed (F1 hybrid) of the *Lactuca* plant.

3. The method according to claim 1, wherein each of the pollen parent of the *Lactuca* plant, the seed parent of the *Lactuca* plant, and a progeny plant resulting from the *Lactuca* plant seed is *Lactuca sativa*.

4. The method according to claim 1, wherein the *Megachile* bee is *Megachile rotundata*.

5. The method according to claim 1, wherein the selected minor nectar plant has a flowering habit in which a flowers of the selected minor nectar plant are opened when the flowers of the pollen parent of the *Lactuca* plant and the seed parent of the *Lactuca* plant are closed.

6. The method according to claim 1, wherein the selected minor nectar plant is at least one species selected from the group consisting of *Anthemis tinctoria*, *Coriandrum sativum*, *Hyssopus officinalis*, *Monarda didyma*, *Nepeta cataria*, *Pentapetes phoenicaea*, *Salvia azurea*, *Erigeron karvinskianus*, *Foeniculum vulgare*, *Melampodium paludosum*, *Portulaca grandiflora*, and *Torenia fournieri*.

7. The method according to claim 1, wherein the selected minor nectar plant is at least one species selected from the group consist of *Erigeron karvinskianus*, *Foeniculum vulgare*, *Melampodium paludosum*, *Portulaca grandiflora*, and *Torenia fournieri*.

8. The method according to claim 1, wherein the selected nectar plant is at least one species selected from the group consisting of *Melampodium paludosum* and *Torenia fournieri*.

9. The method according to claim 1, wherein the selected minor nectar plant is *Melampodium paludosum*.

10. A method of pollinating a *Lactuca* plant via a *Megachile* bee to cross the *Lactuca* plant, the method comprising the steps of:

planting a pollen parent of the *Lactuca* plant;

planting a seed parent of the *Lactuca* plant near the pollen parent of the *Lactuca* plant;

selecting a minor nectar plant based on a preference in flower visiting by the *Megachile* bee, the preference of the *Megachile* bee for flowers of the selected minor nectar plant being equal to or less than a preference of the *Megachile* bee for flowers of the *Lactuca* plant;

positioning the selected minor nectar plant at a location adjacent each of the pollen parent of the *Lactuca* plant and the seed parent of the *Lactuca* plant;

providing the *Megachile* bee;

and pollinating the pollen parent of the *Lactuca* plant and the seed parent of the *Lactuca* plant via the *Megachile* bee when the selected minor nectar plant is present with the pollen parent of the *Lactuca* plant and the seed parent of the *Lactuca* plant so as to cross the *Lactuca* plant, wherein the selected minor nectar plant is at least one selected from the group consisting of an *Anthemis* plant, a *Coriandrum* plant, a *Hyssopus* plant, a *Monarda* plant, a *Nepeta* plant, a *Pentapetes* plant, a *Salvia* plant, a *Erigeron* plant, a *Foeniculum* plant, a *Melampodium* plant, a *Portulaca* plant, and a *Torenia* plant, the pollen parent of the *Lactuca* plant, the seed parent of the *Lactuca* plant, and the selected minor nectar plant grow simultaneously during production of the *Lactuca* plant seed, and the seed parent of the *Lactuca* plant is a male sterile line.

11. The method according to claim 10, wherein a crossing of the *Lactuca* plant is for obtaining (F1) hybrids of a first filial generation of the *Lactuca* plant.

12. The method according to claim 10, wherein each of the pollen parent of the *Lactuca* plant, the seed parent of the *Lactuca* plant, and a progeny plant resulting from a seed of the crossed *Lactuca* plant is *Lactuca sativa*.

13. The method according to claim 10, wherein the *Megachile* bee is *Megachile rotundata*.

14. The method according to claim 10, wherein the selected minor nectar plant has a flowering habit in which the flowers of the selected minor nectar plant are opened when the flowers of the pollen parent of the *Lactuca* plant and the seed parent of the *Lactuca* plant are closed.

15. The method according to claim 10, wherein the selected minor nectar plant is at least one species selected from the group consisting of *Anthemis tinctoria, Coriandrum sativa, Hyssopus officinalis, Monarda didyma, Nepeta cataria, Pentapetes phoenicea, Salvia azurea, Erigeron karvinskianus, Foeniculum vulgare, Melampodium paludosum, Portulaca grandiflora*, and *Torenia fournieri*.

16. The method according to claim 10, wherein the selected minor nectar plant is at least one species selected from the group consisting of *Erigeron karvinskianus, Foeniculum vulgare, Melampodium paludosum, Portulaca grandiflora*, and *Torenia fournieri*.

17. The method according to claim 10, wherein the selected minor nectar plant is at least one species selected from the group consisting of *Melampodium paludosum* and *Torenia fournieri*.

* * * * *